(12) United States Patent
Shushunov

(10) Patent No.: US 10,016,573 B2
(45) Date of Patent: Jul. 10, 2018

(54) SYSTEMS AND METHODS FOR BODY TEMPERATURE MANAGEMENT

(71) Applicant: Anatoly Mayburd, Alexandria, VA (US)

(72) Inventor: Sergei Shushunov, Glencoe, IL (US)

(*) Notice: Subject to any disclaimer, the term of this patent is extended or adjusted under 35 U.S.C. 154(b) by 871 days.

(21) Appl. No.: 14/095,104

(22) Filed: Dec. 3, 2013

(65) Prior Publication Data

US 2015/0151073 A1  Jun. 4, 2015

(51) Int. Cl.
*A61M 16/10* (2006.01)
*A61M 16/00* (2006.01)
(Continued)

(52) U.S. Cl.
CPC .... *A61M 16/1075* (2013.01); *A61M 16/0045* (2013.01); *A61M 16/10* (2013.01); *A61M 16/12* (2013.01); *A61M 16/14* (2013.01); *A61M 2016/103* (2013.01); *A61M 2021/0066* (2013.01); *A61M 2202/0225* (2013.01); *A61M 2205/3368* (2013.01); *A61M 2205/36* (2013.01); *A61M 2205/3606* (2013.01);
(Continued)

(58) Field of Classification Search
CPC .............. A61M 16/00; A61M 16/0003; A61M 16/0051; A61M 16/10; A61M 16/104; A61M 16/1045; A61M 16/1075; A61M 16/108; A61M 16/1085; A61M 16/109; A61M 16/1095; A61M 2016/103; A61M 5/42; A61M 2021/0066; A61M 2205/3368; A61M 2205/3372; A61M 2205/36; A61M 2230/50

USPC ........... 128/204.17, 200.24, 202.16, 204.15, 128/204.18, 204.22, 204.23
See application file for complete search history.

(56) References Cited

U.S. PATENT DOCUMENTS

| | | | |
|---|---|---|---|
| 6,983,749 B2 * | 1/2006 | Kumar | A61K 33/00 128/200.14 |
| 2003/0131844 A1 | 7/2003 | Kumar | |

(Continued)

OTHER PUBLICATIONS

Polderman, et al., "Therapeutic hypothermia and controlled normothermia in the intensive care unit: Practical considerations, side effects, and cooling methods", Credi Care Med. Mar. 2009, 37(3).

(Continued)

*Primary Examiner* — Colin W Stuart
(74) *Attorney, Agent, or Firm* — Thomas | Horstemeyer, LLP

(57) ABSTRACT

A system and method of body temperature regulation, including inhalation of cooled or warmed air flow supplied either manually or by a ventilator through an intubation tube or a breathing mask. The system is automatically regulated to produce a regime of compensated hyperventilation defined as the rate of breathing gas supply that would cause the defined decrease of $CO_2$ blood levels if left uncompensated under given conditions. The system relies on minimized thermal inertia by including a combined heating/warming chamber, where the corresponding heating and cooling paths are mutually insulated. The inhaled breathing gas is automatically directed via a heating or cooling path by a processor, analyzing the inputs of temperature and $CO_2$ level sensors measuring the core body temperature and $CO_2$ blood level.

22 Claims, 5 Drawing Sheets

(51) Int. Cl.
*A61M 16/14* (2006.01)
*A61M 21/00* (2006.01)
*A61M 16/12* (2006.01)

(52) U.S. Cl.
CPC ............... *A61M 2205/366* (2013.01); *A61M 2205/3673* (2013.01); *A61M 2205/8206* (2013.01); *A61M 2205/8262* (2013.01); *A61M 2205/8268* (2013.01); *A61M 2205/8293* (2013.01); *A61M 2230/432* (2013.01); *A61M 2230/50* (2013.01)

(56) References Cited

U.S. PATENT DOCUMENTS

| | | | |
|---|---|---|---|
| 2007/0225623 A1* | 9/2007 | Freeman | A61H 31/004 601/41 |
| 2008/0039735 A1* | 2/2008 | Hickerson | A61B 5/7445 600/532 |
| 2008/0215002 A1 | 9/2008 | Rozenberg | |
| 2008/0262377 A1* | 10/2008 | Belson | A61F 7/0085 600/549 |
| 2009/0156976 A1* | 6/2009 | Korbling | A61M 1/3681 604/5.02 |
| 2011/0005522 A1 | 1/2011 | Marinus | |
| 2012/0226337 A1* | 9/2012 | Tissier | A61F 7/12 607/105 |
| 2013/0030411 A1 | 1/2013 | Kreck | |
| 2013/0090708 A1* | 4/2013 | Dabrowiak | A61F 7/12 607/105 |
| 2014/0350648 A1* | 11/2014 | Ericson | A61M 16/04 607/105 |
| 2015/0151073 A1 | 6/2015 | Shushunov | |

OTHER PUBLICATIONS

Weinrauch, et al., "Beneficial effect on mild hypothermia and detrimental effect of deep hypothermia after cardiac arrest in dogs", Stroke 23, No. 10 (1992): 1454-1462.

Steiner, et al., "Effect and feasibility of controlled rewarming after moderate hypothermia stroke patients with malignant ingarction of the middle cerebral artery", in Stroke Dec. 1, 2001:32(12):2835-5.

Finely, et al., "A comparison of cooling techniques to treat cardiac arrest patients with hypothermia" Stroke Res. Treat Jul. 25, 2011.

Larsson, et al., "Cold saline infusion and ice packs alone are effective in inducing and maintaining therapeutic hypothermia after cardiac arrest", Resuscitation, ScienceDirect, 2010.

Mikkelsen, et al., "Use of Therapeutic Hypothermia After In-Hospital Cardiac Arrest", Critical Care Medicine, 2013.

* cited by examiner

Figure 3: Freezer Model/Schematic. The temperature of the air at the various points i.e., T ambient, T inside freezer and T airout freezers is measured by thermistors TC1, TC2, TC3 and TC4 respectively. The flow rate of air flowing into the freezer is measured by a flow meter Experimental results as compared to Theoretical Predictions. Air through freezer maintained at -40C at 60 LPM with tube lengths ranging from 0.25 to 5 meters.

SYSTEMS AND METHODS FOR BODY TEMPERATURE MANAGEMENT

BACKGROUND

Therapeutic hypothermia, or total body cooling, is a treatment method used to prevent or minimize brain injury following cardiac arrest, stroke, neonatal encephalopathy, or traumatic head injury. The typical goal of such therapy is to reduce the body temperature to approximately 33-34° C. as quickly as possible. The best outcomes normally can be achieved when the induction of hypothermia occurs within the first one or two hours following injury.

Several different therapeutic hypothermia solutions have been introduced. Generally speaking, the solutions may be categorized as invasive or non-invasive methods. Invasive methods include using cooling endovascular catheters tipped with a balloon through which cold water flows, irrigating the body cavity with cold water, intravenous infusion of cold fluids, and using an extra corporeal membrane oxygenation (ECMO) circuit for cooling blood. Non-invasive methods include using cooling blankets through which cooling liquids flow, emulating emersion of the patient in ice water using perforated polymer sheets, and injecting volatile cooling liquids within the nasal cavity that quickly evaporate.

Each current therapeutic hypothermia method has one or more drawbacks. Such drawbacks include the potential for side effects, the requirement for skilled staff to perform the methods, inadequate rates of cooling, and heavy and expensive equipment. Moreover, current invasive and non-invasive methods are limited to use in hospital settings and patients have limited access to them.

The publication US2013090708A discloses devices and methods for cooling all or part of the body of a human or animal subject by inserting a heat exchange catheter into the subject's body and infusing into or through the catheter a heat exchange medium that contains liquid phase matter and frozen solid phase matter, wherein at least some of the solid phase matter melts while in the catheter. Yet, endovascular cooling catheters do not provide fast heat loss. They produce cooling rate similar to cooling body wraps. Endovascular cooling catheters are invasive, require use of systemic anticoagulation and specially trained staff all making them unsuitable for out of hospital use. The adverse effects include bleeding, infection, vascular puncture, and deep vein thrombosis.

The publication WO04089444A1 discloses use of Extra-corporeal Membrane Oxygenation for rapid body temperature management. ECMO allows very rapid rate of heat loss by pumping blood through a cooler. However, ECMO is invasive and requires presence of a highly trained staff and systemic anticoagulation. ECMO requires a longer time to start than the less invasive methods and is associated with significant side effects, including bleeding, infection, deep vein thrombosis and stroke. It is unsuitable for out of hospital use.

The publication "Cold saline infusion and ice packs alone are effective in inducing and maintaining therapeutic hypothermia after cardiac arrest", Larsson I M, Wallin E, Rubertsson S, Resuscitatio, 2010; 81:15-19) discloses intravenous or intraosseus infusion of cold saline producing fast heat loss and is inexpensive, but it requires administration of non-physiologically large and dangerous volumes of fluids, which can lead to respiratory and/or cardiac failure. In addition, it does not allow precise control of temperature reduction or maintenance.

The publication U.S. Pat. No. 5,005,374A discloses a thermal wrap including a fabric band having a thermally insulating outer layer and a non-insulating inner layer. A cavity is formed between the two layers for receiving a flexible cold pack containing deionized water and a chemical freezing agent. In one embodiment, the fabric band is in the form of a collar to be worn about the individual's neck or other body part. In another embodiment, the fabric band is in the form of a jacket for surrounding a beverage container such as a wine bottle. Cooling body wraps do not provide fast heat loss and require 4 to 8 hours to achieve target temperature, depending on many factors, including the amount of subcutaneous fat. Cooling units are relatively large and are not suitable for out of hospital use. Controlled re-warming is not precise, access to the patient is restricted.

The publication US20020007201A discloses methods and devices for extracting thermal energy from the body core of a subject. A limb or portion is placed in a sealed enclosure to produce an enclosed portion of the subject. A surface of the enclosed portion of the subject is then contacted with a low temperature medium under negative pressure conditions for a period of time sufficient to provide for the desired core body thermal energy extraction. The subject methods and devices find use in a variety of applications, e.g. providing relief from temperature sensitive disorders, such as multiple sclerosis, and the treatment of hyperthermia, among other treatments. A cold water immersion imitating device offers high rate of heat loss and fast cooling. The drawbacks include extremely large size, restriction of access to the patient, inability to use in pre-hospital settings.

The publication US20130030411A discloses irrigation of nasal cavity with coolant device and is a non-invasive technique. Although the irrigation device is compact and can be used in pre-hospital settings, it does not provide fast heat loss, or controlled re-warming and the use is known to produce thermal injury to the nose.

The publication US20080215002A discloses a method for cerebral and systemic cooling by circulating a cold liquid through a nasal catheter looped through the patient's nasal cavities and around the nasal septum. The nasal catheter is inserted into the patient's first nostril, advanced through the nasal cavity, around the nasal septum and out of the patient's second nostril. A cold fluid having a temperature between about −20° C. and about 37° C. is flowed though a lumen in the nasal catheter to cool the nasal cavity. The nasal catheter may have one or more flexible balloons mounted on the catheter such that when the catheter is looped around the nasal septum, the balloon(s) are positioned in a portion of the patient's first and second nasal cavities. When a cold liquid is circulated through the catheter lumen, the flexible balloons expand to a contact the inner walls of the nasal cavities and provide direct cooling of the nasal cavities. Intranasal balloon tipped cooling catheter is portable. Yet it does not allow fast cooling or controlled re-warming.

In view of such drawbacks, it can be appreciated that it would be desirable to have an alternative system and method for inducing therapeutic hypothermia. One such method is inhalation of cold gases utilizing high heat transfer surface of alveoli. The method offers simultaneous unhindered access to the head and body surface of the patient, allowing intense therapy to proceed simultaneously with the hypothermia induction. Such methods are exemplified by US20030131844 A1 disclosing methods of cooling and warming the human being body. Using the described method, the body may be cooled from normal physiological temperature (37° C.) to lower temperatures, or from an elevated body temperature to a normal physiological temperature. The method may also be used to warm a cold body back to normal physiological temperature. The lungs are used as a heat exchange source for cooling and heating the body. Helium, mixed with air or oxygen in varying concentration, can be used as the heat transfer medium. Cooling devices and heating elements connected to the breathing circuit heat or cool the inspired gases as required. Atomized liquid may be added to the gas stream to use evaporative heat loss from the liquid, for example, perfluorocarbons, administered into the lungs. When cooling the body, medications can be administered to suppress reflex heat production. Hypothermia may be terminated and the body rewarmed in some methods by raising the temperature of the helium-oxygen mixture, for example, up to 55° C. During rewarming, the inspired gases may be humidified to minimize evaporative heat loss from the lungs. Pharmacological agents that depress heat production may be discontinued, if clinical situations permit, to allow the body to regenerate heat. The methodology to induce and maintain hypothermia in humans and other human beings includes: (1) use of lungs for heat exchange; (2) use of cooled gases for ventilation; (3) use of helium in the ventilation gas mixture; (4) use of liquid atomized perfluorocarbons to achieve evaporative cooling from the lungs; and (5) use of medications to control reflex heat production. Hypothermia is achieved through loss of heat from the lungs. The presence of helium tanks, valves and expense of helium not being recirculated makes the system costly and limit its application scale. The presence of breathable fluorocarbon also required additional equipment, environmentally harmful in case of mass application and requires additional cooling facilities either to maintain the Freon fluid or to produce it by adiabatic expansion. The fluorocarbon mists can damage nasal mucosa, cause bleeding and frost-bites due to the bulk of heat transfer occurring in the nasal passages and not along the entire heat-exchange path in lungs, which rely on extremely extended surface of heat exchange (100-120 m$^2$) and therefore do not rely on high temperature gradient or traumatic rate of heat transfer. The heat transfer cannot be precisely controlled.

The publication US20110005522 A1 discloses a device for providing a breathing gas, the device comprising gas supply and gas conditioning. The breathing gas is conditioned by forming particles comprising a frozen fluid in the breathing gas. The breathing gas and the particles will be warmed by the body of the patient, preferably to a temperature at which the frozen fluid melts. The device may comprise cooling elements to freeze water into bodies of ice, or the device may comprise a space for storing bodies of ice formed outside the device, for example in a separate fridge. The device may further comprise automatic means for crunching the bodies of ice into small particles or for example a rasp for grating the body of ice to generate small particles, which particles are then added to the flow of breathing gas. The presence of ice particles limits the method in many respects: a) The bronchioles and alveoli will be flooded upon melting of the ice, limiting gas exchange ($O_2$ and $CO_2$), the patient will be suffering from iatrogenic drowning, unless the circuit is not interrupted frequently for removal of water condensate) b) The contact with the bigger particles will cause local tissue damage and irritation, including bleeding due to the same factors as considered for fluorocarbons c) temperature control is difficult.

According to our study of the problem, the existing body cooling and re-warming systems are impractical and functionally cumbersome. The reality is reflected in the fact that only 2% of the situations where mild therapeutic hypothermia would cause therapeutic benefits (stroke, brain trauma, infections) lead to actual implementation of cooling methods (see Mikkelsen M E et al. in "Use of therapeutic hypothermia after in-hospital cardiac arrest" Crit Care Med. 2013 June; 41(6):1385-95). The continuous scarcity of the inexpensive, practical and versatile devices and methods that can be applied within and outside of hospital setting, during transportation or in ambulatory setting invalidates the very idea of therapeutic hypothermia.

Without being bound by a theory, we have surprisingly discovered that passing of the breathing gas through a sufficiently long and heat-conductive path in a cooler enables it to cause hypothermia or re-warm the patient within a short time interval. The resulting device is simple, robust and inexpensive. The device does not rely on special gas mixes and is compatible with diverse sources of cooling or warming. The temperature control is very reliable and operable in a narrow range. Thus, a superior apparatus and method of application to cause rapid patient hypothermia and re-warming constitute the invention. The heat exchange is mild and physiological and relies on extended surface of heat transfer and low coefficient of heat transfer, thus avoiding local cold trauma. We termed the method "Body temperature management" owning to its versatility.

BRIEF DESCRIPTION OF THE DRAWINGS

The present disclosure may be better understood with reference to the following figures. Matching reference numerals designate corresponding parts throughout the figures, which are not necessarily drawn to scale.

SUMMARY

Figure 1:
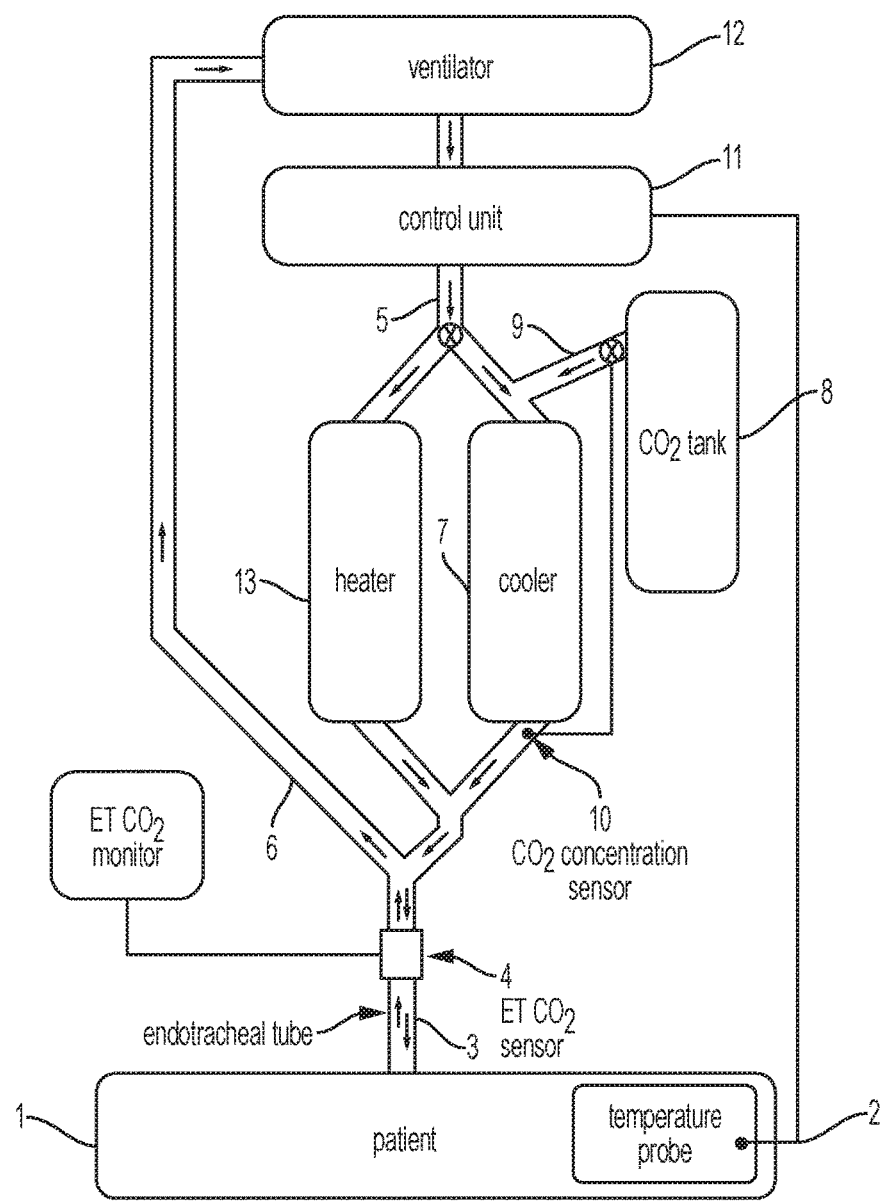
FIG. 1 is the general overview of the system for body temperature management

Disclosed herein is an apparatus and method for inducing therapeutic hypothermia that is based upon the administration of cold breathable gas to the lungs. This new physiological approach addresses many of the shortcomings of existing methods of induction of hypothermia and existing hypothermia induction equipment. One of the most important aspects of therapeutic hypothermia therapy is reducing the body temperature as quickly as possible. It is believed that using cold gas ventilation induces hypothermia more quickly than cooling blankets, which is currently the most commonly used method for inducing therapeutic hypothermia. The law of cooling states that the rate of heat loss of an object is proportional to the difference in temperatures between the object and its surroundings and the contact surface area.

In some embodiments, breathable gas (e.g., air, oxygen, or both) is cooled to a very low temperature and delivered to a patient using a ventilator (or by a self-inflating bag). As the cold gas is inhaled by the patient, heat transfer occurs within the lungs that lowers the body temperature of the patient. In some embodiments, the gas supplied to the patient is cooled to a temperature well below 0° C.

Cooling depends on a heat transfer coefficient, i.e., a unique number that reflects physical properties of the media. There are theoretical advantages of using lung air/oxygen cooling over skin water cooling. First, there is a much greater surface area of the lungs as compared to the surface area of the skin. Lung surface area in adults is approximately 120 m$^2$ as compared to 1.8 m$^2$ for the skin surface. Practically speaking, external cooling devices are typically applied to only about 50% of the body surface (primarily thighs, abdomen and low chest), which equates to only 0.9 m$^2$ of surface area. Second, air/oxygen temperature can be decreased well below 0° C. as compared with water, which becomes solid at 0° C.

The cold gas hypothermia provides the advantages of being minimally invasive (because it will utilize artificial airway and mechanical ventilation always necessary in patients with conditions treatable by hypothermia) to reduce spectrum of potential complications, unobtrusive so as to provide convenient access to the patient, portable so as to be usable in pre-hospital settings, effective so as to provide a rapid rate of heat loss, and simple so that it can be performed by someone without extensive training.

In some embodiments, cooling and warming processed are conducted in a single apparatus. In some embodiments, the thermal inertia of the cooling and heating conduits is minimized. In some embodiments, the thermal inertia of cooling and heating conduits is overcome by passing the cooled and warm gas flows through alternative routes operating in complete absence of heat transfer between the conduits in the same device. In some embodiments the intensity of heat exchange between lungs and gas is regulated by hyperventilation with a hyper cold air, defined as air at the temperatures below 0° C., −20° C., −30° C., −40° C. without limitations. In some embodiments, the processes of hypothermia induction and rewarming are conducted on the local time-scale, with several inhalation cycles per a cold conduit followed by a computed number of inhalations per a warmed conduit. In some embodiments only re-warming aspect of the method is implemented.

DETAILED DESCRIPTION

FIG. 1 presents the general overview of the system for body temperature management. The temperature of the patient 1 who typically experiences a life-threatening condition is monitored by a temperature probe 2. The breathing gas is supplied through an intubation tube 3 with the connected End-Tidal CO$_2$ (ETCO$_2$) monitor, the said CO$_2$ being admixed by the conduit from the tank 8 in the cooling conduit via the path 9 through a valve, controlled by the CO$_2$ sensor 10. The switch valve 5 directs the flows of the breathing gas through the cooler or the heater. The path 6 is the exit path of the breathing gas leaving the intubation tube. The cooler conduit 7 is coupled with the heater 13 in a single sub-unit wherein the cooling and heating paths are thermally isolated. The control unit 11 is provided to regulate the volume and sequence of the breathing gas flows through the cooler/heater subunits 7 and 13. Ventilator 12 provides breathing gas flow according to determined settings.

In operation, the inputs of the sensors 2, 4 and 10 are all integrated by a microprocessor determining the splitting ratio and the sequence of passing through the cooled 7 and heated 13 conduits of the cooling/heating subunit, and the concentration of carbon dioxide in the inhaled breathing gas. The breathing gas is supplied by the ventilator 12 through the control unit 11 through control valve 5 either into the cooler 7 or heater 13, enters the intubation tube and leaves the patient through the path 6. The amount of the added CO$_2$ is integrated with the amount of the exhaled CO$_2$ based on the data of the ETCO$_2$ 4 and the inspired CO$_2$ sensor 10.

Notably, breathing cold air in ordinary situations does not produce hypothermia. However, in ordinary situations persons breathing cold air (e.g., when outside in cold climates) are usually wearing protective clothing, have higher heat production due to physical activity, and do not receive sedatives and/or neuromuscular blocking agents that produce vasodilatation and prevent reactive shivering responsible for muscle heat production as is often the case when therapeutic hypothermia is performed for patients with cardiac arrest, severe head injury and stroke, or other life threatening conditions.

As is well known, patients undergoing anesthesia for surgical procedures are prone to develop hypothermia due to changes in thermoregulation even when ventilated by gas at room temperature. Thermoregulation in critically ill patients receiving sedatives, narcotics, and neuromuscular blocking agents is not dissimilar to thermoregulation in patients undergoing anesthesia. The reason accidental hypothermia is not commonly observed in intensive care setting is because of the widespread use of active heat exchangers in conjunction with mechanical ventilators. It is believed that in critically ill, comatose, or sedated and mechanically ventilated patients, replacement of the heat exchanger with a gas cooling device would rapidly induce hypothermia.

Figure 2:
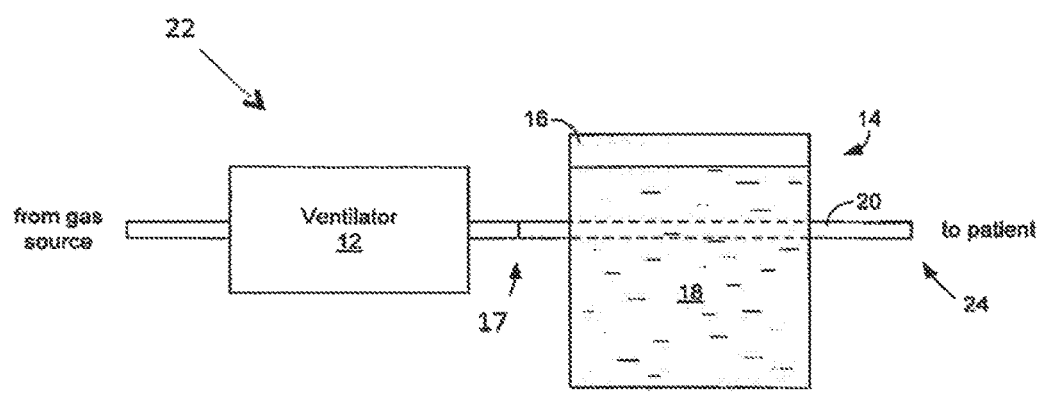
FIG. 2 is a block diagram of an embodiment of an air cooling route for a system for inducing therapeutic hypothermia.

FIG. 2 is a block diagram of an embodiment of an air cooling route for a system for inducing therapeutic hypothermia (system 22). As is shown in FIG. 2, the system 22 generally includes a ventilator 12 and a cooling unit 14. The ventilator 12 can in some embodiments be of conventional design and is used to mechanically move breathable gas (air, oxygen, or both) from a gas source (e.g., air from the surrounding environment) into and out of the lungs to provide the mechanism of breathing for a patient who is unable to breathe on his or her own or who is having difficulty breathing.

The cooling unit 14 is adapted to receive gas from the ventilator 12, cool it to a low temperature, and deliver it to the patient. In some embodiments, the cooling unit 14 comprises a freezer that has one or more internal cooling elements. As is shown in FIG. 2, the cooling unit 14 comprises an interior chamber 16 in which a cooling medium 18 is contained. The size of the cooling unit 14 and its interior chamber 16 may depend upon the particular application. For instance, if the system 22 is intended for use in the field, the cooling unit 14 and its interior chamber 16 can be relatively small to facilitate portability. By way of example, the cooling unit can occupy a volume of no more than approximately 1 cubic foot. In more permanent applications, the cooling unit 14 and its interior chamber 16 can be larger. Regardless, the system 22 can be constructed to be significantly smaller, lighter weight, and less expensive than current therapeutic hypothermia systems.

In some embodiments, the cooling medium 18 comprises a liquid cooling medium that freezes at a temperature well below 0° C. Example cooling media include salt solutions, such as a calcium chloride (CaCl$_2$) solution, a sodium chloride (NaCl) solution, a magnesium chloride (MgCl$_2$) solution; alcohol solutions, such as an ethylene glycol solution; refrigeration coolants, such as fluorocarbon coolants; thermoelectric cooling and other cooling media.

Extending through the interior chamber 16 of the cooling unit 14 is tubing 20 that includes an inlet 17 upstream of the unit and an outlet 24 downstream of the unit. As is shown in FIG. 2, a section of the tubing 20 is immersed within the cooling medium 18 within the interior chamber 16 so as to provide maximum heat exchange. During use, gas from the gas source is drawn in by the ventilator 12 and is delivered to the inlet 17 of the tubing 20. The gas then passes through the segment of the tubing 20 that is immersed in the cooling medium 18. During its passage through that segment of the tubing 20, the gas is rapidly cooled to a much lower temperature. By way of example, if the cooling medium 18 is maintained at a temperature at or near approximately −40° C., the gas can be cooled to a temperature at or near −30° C. In some embodiments, this can be achieved with a segment of tubing immersed in the cooling medium 18 that is one foot or longer in length. The cooled air then exits the tubing 20 from the outlet 24 and is delivered to the patient.

In some embodiments of therapeutic hypothermia induction the tubing 20 enters an intubation tubing. Endotracheal intubation (ET) is a relatively simple procedure that can often be performed by paramedics in the field. Respiratory arrest follows cardiac arrest within seconds. The only way to assure good ventilation and oxygenation is to establish artificial airway (ET tube). This procedure does not require penetrating natural barriers, (skin or mucous membranes), making it less invasive than placing needles or catheters into enclosed body cavities. Because just about 100% cardiac arrest patients get intubated, induction of hypothermia using lungs (through previously placed ET tube) is just an opportunistic way of doing something invasive without adding invasivity.

In some embodiments related to therapeutic hypothermia, re-warming is performed through the same path as hypothermia, including intubation tube. Yet in other embodiments such as accidental hypothermia the re-warming subject is capable of breathing independently and a face mask is sufficient.

Figure 3:
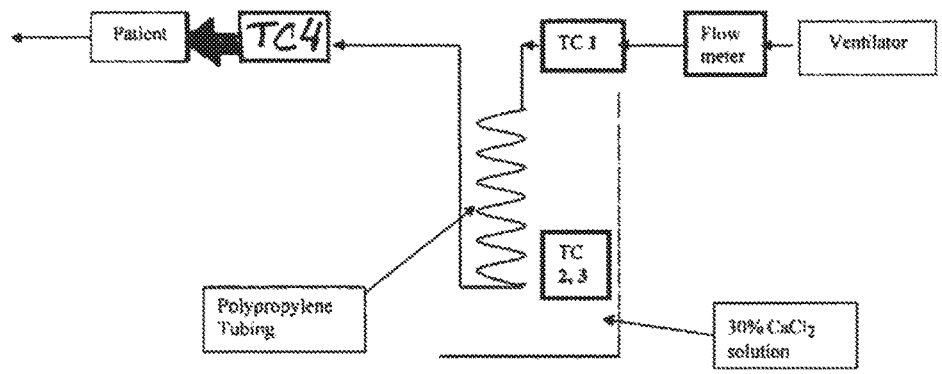
FIG. 3 is a more detailed schematic of a freezer module.

FIG. 3 presents a more detailed schematic of a freezer module, where TC1 represents temperature control point on the entry to the heat exchanger, TC2 and TC3 represents temperature control in the cooling fluid, TC4 represents temperature control on the exit of the cold fluid tank.

The system 22 of FIG. 2 can be altered in many ways. For example, although the cooling unit 14 has been shown as being downstream from the ventilator 12, the cooling unit 14 could be integrated into the ventilator 12, if desired. Furthermore, although the system 22 is shown as including the ventilator 12, the cooling unit 14 could instead be used with a manually-operated ventilation device, such as a bag mask. In such a case, the bag mask would draw in cold gas from the cooling unit 14 for delivery to the patient. In most cases, the patient will need to be rewarmed after the body temperature has been reduced as a result of the inducement of therapeutic hypothermia. In some embodiments, the system 22 can incorporate a thermal control unit (any commercially available heat and moisture exchanger) that provides for both cooling and heating of gas that is delivered to the patient, so that the patient can be initially cooled with the system, and later rewarmed by the same system.

Figure 4:
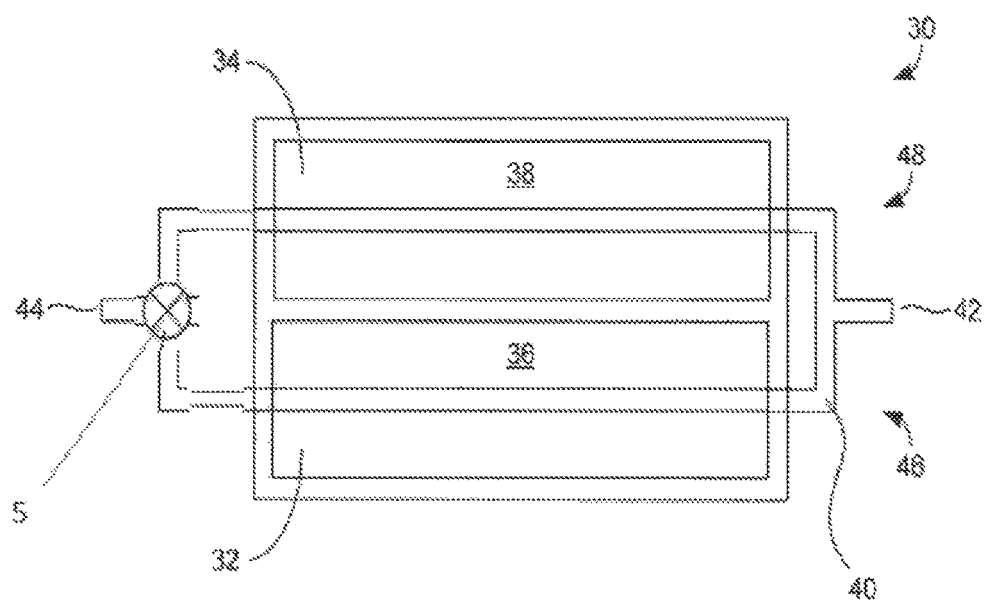
FIG. 4 is a block diagram of a thermal control unit that can be used in a system for inducing therapeutic hypothermia and re-warming alternatively

FIG. 4 is a block diagram of a thermal control unit that can be used in a system for inducing therapeutic hypothermia and re-warming alternatively, corresponding to a detailed view of the elements 5, 7 and 13 in FIG. 1. FIG. 4 illustrates an embodiment of a thermal control unit 30 that can be used in this manner. As is shown in FIG. 4, the unit 30 comprises two mutually insulated chambers, a cooling chamber 32 and a heating chamber 34. The cooling chamber 32 contains a cooling medium 36 and the heating chamber 34 contains a heating medium 38. Tubing 40 is associated with the unit 30 and comprises an inlet 42 and an outlet 44. Provided between the inlet 42 and the outlet 44 are a cooling branch 46 and a heating branch 48 that pass through the cooling chamber 32 and the heating chamber 34, respectively. In the illustrated embodiment, both the cooling and heating branches 46, 48 include electronically-controlled valve 5 that can be actuated to control the flow of air from each of the branches to the outlet 44 of the tubing 40. In some embodiments, the actuation of the valve 5 can be controlled by a processor associated with the unit 30 in response to feedback received from one or more sensors that are used to monitor a patient parameter (e.g., core temperature) and/or the temperature of the gas that is delivered to the patient.

In some embodiments, the unit 30 comprises a modular assembly of sub-units: portable modular Temperature Management Device (TMD, consisting of Cooler (C), Heat and Moisture Exchanger (HME) (any existing model), control unit (CU) to direct air into either C, or HME and $CO_2$ source to compensate for hyperventilation induced hypocarbia. The extent of potential hypocarbia varies depending on the patent's weight, current intensity of metabolism and physiological condition, but (in the absence of compensation) could reach non-physiological values if $CO_2$ is not supplied. Non-limiting exemplary values of $pCO_2$ that could be reached if compensation $CO_2$ flow is not supplied are 35 torr, 25 torr, 20 torr, 15 torr and 10 torr. Such a regime was termed "compensated hyperventilation" The cooler can be used independently from HME, with or without HME being attached. In this shape it will work as a very compact and portable cooler based on either pump refrigeration of coolant surrounding tube or on thermo-electric principle. HME can be used with or without C attached to the circuit as a warmer. When C is used in parallel with HME the device will be used either as Cooler, or as a temperature management device (just enter desired temperature through a control panel on CU and let it do the work by selecting path of air flow).

In operation, the modular embodiment of the unit 30 will provide a very stable temperature regime, which is vital for success of hypothermia treatment, due to the possibility of canceling the thermal inertia factors. Excessive hypothermia leads to inhibition of cardiac output and to immunosuppression. Furthermore, re-warming after excessive hypothermia leads to the same mortality rates as are observed in no hypothermia at all. However, use of mild hypothermia leads to substantially decreased mortality possibly via minimization of inflammatory effect of trauma or stroke. In this context, current devices are either incapable of providing steady temperature management (they cool, but do not maintain target temperature) or are not accurate (cooling blanket) either overcooling or undercooling, causing substantial temperature fluctuations, which are very deleterious: elevations cause increased intracranial pressure (more injury), decreases below the target range depress cardiac contractility and immune system. This TMD will allow body temperature control within very narrow range when CU, receiving core temperature feedback will decide where to send the air: to cooler or warmer. Typical re-warming takes 12 hours, sometimes 24. It must be steady: bringing temperature from 33 to 37° C. evenly over 12 hours means that it must be increased by 0.3° C. every hour. More rapid or less controlled re-warming can produce undesirable spikes in intracranial pressure, so that the process could have to be temporarily halted or perhaps reversed instantly. The device with readily available heating and cooling chambers is adapted for rapid and precise intervention.

In some embodiments, the feedback to TMD is supported by placement of endothermometer sensors in the urinary bladder, esophagus or both, the disclosure being only exemplary without limiting any other modes of placement.

In some embodiments, the control parameter is inhalation, and the heat regime comprises a repeated cycle of inhaling through the cooling and warming paths. The frequency of cold (via branch 46) and warm (via branch 48) passages determines the resulting temperature, with the benefit of maintaining minimal heat inertia of the corresponding heat paths so that the temperature can be rapidly adjusted based on the feedback temperature sensors, well known to the skilled in the art. The rate of cooling in therapeutic hypothermia minimizes frequency of complications, according to the study by Polderman K H et al. in "*Therapeutic hypothermia and controlled normothermia in the intensive care unit: practical considerations, side effects, and cooling methods*" published in Crit Care Med. 2009 March; 37(3): 1101-20. In this study, hypothermia is being used with increasing frequency to prevent or mitigate various types of neurologic injury. In addition, symptomatic fever control is becoming an increasingly accepted goal of therapy in patients with neurocritical illness. Rapid induction of mild hypothermia decreases the risks and consequences of short-term side effects, such as shivering and metabolic disorders. A risk of clinically significant arrhythmias occurs only if core temperature decreases below 30° C. Thus, rapid and well-controlled temperature management procedure is required.

It is essential from the point of invention's utility that combining the heating and cooling paths in a single device does not merely produce a compact and modular system, but leads to functional synergy of narrowly controlled body temperature management regime, that can be fine-tuned to achieve fewer complications in hospital and out-of-hospital conditions. Weinrauch et al. in "*Beneficial effect of mild hypothermia and detrimental effect of deep hypothermia after cardiac arrest in dogs.*" Stroke 23, no. 10 (1992): 1454-1462 discloses the functional optimum corresponding to mild hypothermia as compared to normothermia and severe hypothermia. Actually, the latter can even worsen the outcome. Steiner T. et al in "*Effect and feasibility of controlled rewarming after moderate hypothermia in stroke patients with malignant infarction of the middle cerebral artery*" in Stroke 2001 Dec. 1; 32(12):2833-5 discloses moderate hypothermia that has been found to reduce intracranial pressure (ICP) significantly in patients who have severe middle cerebral artery infarction. However, during passive rewarming, ICP continuously rises and some patients suffer transtentorial herniation and almost always-inevitable death. Achievement of rewarming protocol was assessed by hit rate of temperature target intervals. Side effects of hypothermia were assessed. Rates of change of both ICP and CPP were correlated significantly with increase in temperature (ICP r=0.62, P=0.002; CPP r=−0.50, P=0.017). Slow, controlled rewarming is feasible and may be used for ICP and CPP control after moderate hypothermia for space-occupying infarction. Finley C A et al. in "A comparison of cooling techniques to treat cardiac arrest patients with hypothermia" published in Stroke Res Treat. 2011; 2011:690506, Epub 2011 Jul. 25 discloses that In spite of the data and guidelines hospitals in the United States have been slow to adopt therapeutic hypothermia in the routine management of comatose postcardiac arrest patients. This may be in part explained by physician unfamiliarity with therapeutic hypothermia and in part by the labor intensiveness and inaccuracy of surface cooling using ice bags and cooling blankets. Most studies to date have used conventional surface-based cooling techniques (ice bags and cool air or water blankets), which are generally slow and imprecise in achieving and maintaining target temperature. Animal models suggest that a delay in cooling abates the neurological benefits of mild hypothermia and that deep hypothermia has no added benefit over mild-to-moderate hypothermia. These publications are incorporated herein by reference and illustrate the principle of sensitive and rapid thermoregulation as defining therapeutic success.

The embodiments in FIG. 1-5 are not the only possibility within the scope of the invention and should not be construed as limiting. In some embodiments, the heater/cooler elements are based on Peltier thermoelectric principles. The hypothermia apparatus based on Peltier heat-exchange is capable of utilizing the energy of the regular power grid, fuel cells, chemical batteries, supercapacitors, ship engines, truck, train and tank engines, dynamo generators, solar batteries, wind and thermal source energy without limitations, the sources above being enumerated only for illustrative purposes.

In some embodiments, the energy source for the hypothermia apparatus is based on an autonomous power generator, brought in motion by mechanical means, combustion, diesel, solar radiation such that the compact body temperature management system is capable of functioning in rural, remote, mountain, forest, battlefield environments without limitations, the examples above being enumerated only for illustrative purposes.

In some embodiments, the purpose of the system is not induction of hypothermia but instead re-warming. An accumulator fed by a fuel cell, solar battery, wind turbine or engine may be used to warm the inhaled air in the conditions of severe environmental hypothermia or battlefield.

In some embodiments, the purpose of inducing hypothermia or re-warming is treatment of a domestic or a companion animal.

In some embodiments, the supplemented $CO_2$ is also designed to maintain normocarbia (prevent alkalosis) and is added depending on the sensor feedback in the ranges between 0% and 2.0% by volume, between 2.0 and 3.0% by volume, between 3.0 and 4.0% by volume, between 4.0% and 4.5% by volume, between 4.5% and 5.0% by volume, between 5.0% and 5.5% by volume, between 5.5% and 6.0% by volume, between 6.0% and 7.0% by volume, between 7.0% and 8.0% by volume. The specific range is determined by the degree of acidosis or alkalosis.

End Tidal $CO_2$ monitor (attached at the hub of endotracheal tube, very standard device on intubated patients) can send info to electronically controlled $CO_2$ flow meter to regulate $CO_2$ admixture to have ET $CO_2$ within certain range (anywhere 25-35 torr) while patients undergoes compensated hyperventilation. The End Tidal $CO_2$ monitor is mentioned solely for illustrative purposes. Other capnological monitoring sensors can be applied without limitations.

The larger mass of cold gas further enhances the cooling rate. In view of these advantages, it is believed that the disclosed systems will bring standardization to therapeutic hypothermia treatment.

The application of the invention is described in the following non-limiting illustrative

EXAMPLES

Example 1

Feasibility of a Compact Air Cooling Unit

Figure 5:
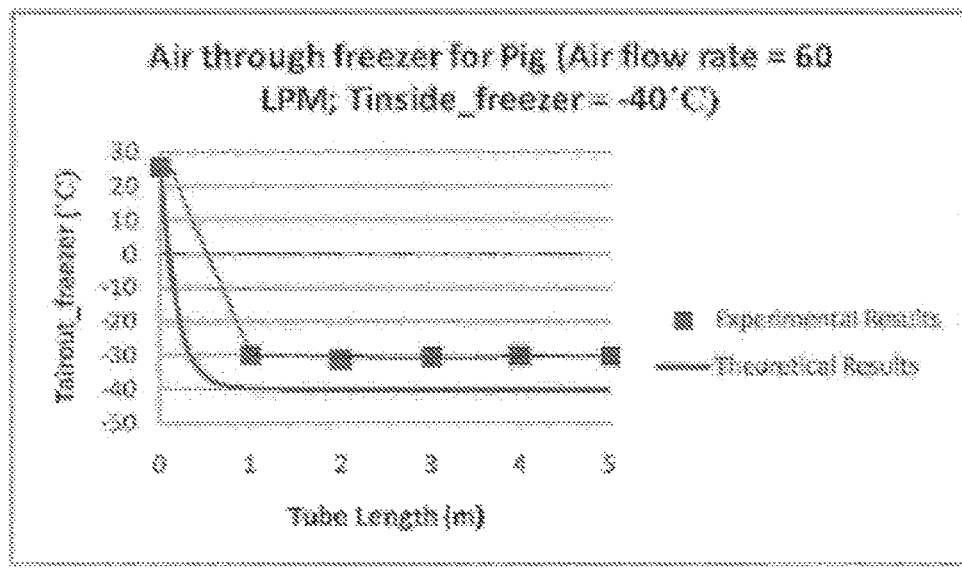
FIG. 5 is graph of experimental results achieved with a prototype system as compared to a simple theoretical model of the system.

A prototype cooling system for use with current hospital ventilators was developed to test the effectiveness of the disclosed systems in cooling ventilator air (FIG. 3). The prototype device was designed to be used to test proof of concept in a large animal model to demonstrate that using cold air ventilation induces hypothermia more quickly than cooling blankets. The prototype system was shown to be capable of cooling room temperature air (−25° C.) to as low as −30° C. with 25 mm diameter plastic tubing of at least one meter in length. For these temperatures, air flow rates can range from 20 liters/minute (LPM) to 70 LPM. The core of the cooling system in the prototype system was a commercial low-temperature freezer with a capacity of 5 cubic feet. An approximately 30 $CaCl_2$/water solution was used as the cooling medium within the freezer. Testing revealed that when the freezer had been running for at least two hours, the air passed through the system was cooled to within 2 to 4° C. of its final temperature within 10 minutes of initiating airflow. The system was tested for two additional hours and was proved to be capable of maintaining a final −30° C. temperature for that time. It is assumed that this temperature can be maintained for several more hours. FIG. 5 shows the experimental results as compared to a simple theoretical model of the system. The theoretical model in this case comprised considering the heart transfer coefficient across the polypropylene tube wall, heat transfer coefficient on the side of the moving air within the tube and the heat transfer in the surrounding cold fluid 18, FIG. 2. As can be appreciated from that figure, the trends are similar, but the actual system may not actually reach the theoretical limit of −40° C. due to imperfect insulation of the system and the relatively warm environment (room air) surrounding the freezer and tubing. Results of the testing indicated that, for commercial product design, the freezer could have a capacity of approximately one cubic foot, and therefore occupy a much smaller space and be much lighter. Furthermore, application of thermoelectric cooling may lead to even more compact apparatus, portable by a single person with ease.

Example 2

Successful Results Observed in Humans

A number of pediatric patients (6 patients, age 5-12 years, weight 20-50 kg) suffering malignant hyperthermia or neuroleptic malignant syndrome were intubated and placed under ventilator at the body temperature reaching 105-106° F. The cool air was provided using 60 cm of the tubing as in the Example 1 submerged in the ice water at 0° C. The final temperature of the air exiting the ice bath and entering the intubation tube was in the range between 5-15° C. The temperature of the exiting air in the regime of normal ventilation (7 liters/minute) was 30° C., however the real exit air temperature could be higher since the stretch between the exhalation branch of the intubation tube and the insertion point of the thermometer was not insulated. Within 30-45 minutes of this regime the patient body reached 98-100° F. All patients survived their condition as a result of the intervention.

Example 3

Comparison with the Reference Model

Factor analysis was conducted to compare the cooling rate potentially observed in air-lung system vs. water blanket system. The latter can be modeled as water-water heat transfer across a heat-conductive obstacle. Average values for the overall heat transmission coefficient through different combinations of fluids on both sides of the wall and type of wall—can be found using the data of Engineering ToolBox at http://www.engineeringtoolbox.com/overall-heat-transfer-coefficients-d_284.html incorporated herein by reference in the Table 1.

TABLE 1

Fluid Transmission Surface Fluid Overall Heat Transmission Coefficient

| Transmission | | | Overall Heat Transmission Coefficient | |
|---|---|---|---|---|
| Fluid | Surface | Fluid | (Btu/ft² hr ° F.) | (W/m² K) |
| Water | Cast Iron | Air or Gas | 1.4 | 7.9 |
| Water | Mild Steel | Air or Gas | 2.0 | 11.3 |
| Water | Copper | Air or Gas | 2.3 | 13.1 |
| Water | Cast Iron | Water | 40-50 | 230-280 |
| Water | Mild Steel | Water | 60-70 | 340-400 |
| Water | Copper | Water | 60-80 | 340-455 |
| Air | Cast Iron | Air | 1.0 | 5.7 |
| Air | Mild Steel | Air | 1.4 | 7.9 |
| Steam | Cast Iron | Air | 2.0 | 11.3 |
| Steam | Mild Steel | Air | 2.5 | 14.2 |
| Steam | Copper | Air | 3.0 | 17 |
| Steam | Cast Iron | Water | 160 | 910 |
| Steam | Mild Steel | Water | 185 | 1050 |
| Steam | Copper | Water | 205 | 1160 |
| Steam | Stainless Steel | Water | 120 | 680 |

Note that these coefficients are very approximate. They depend on the fluid velocities, their viscosity, the condition of the heating surfaces, the size of the temperature differences. Examination of the Table 1 allows setting the ratios of water-water vs. water-gas heat transfer coefficients as ~25:1 fold different. The surface of heat transfer in the lungs is assumed to be ~120 m² being maintained by positive ventilator pressure spreading the alveoli that tend to get closed at lower pressures. The area of heat exchange in cold water submersion is ~1.4 m² leading to the ratios of water-water vs. water-gas heat transfer areas as ~1:100 fold different. The driving force (temperature gradient) in water-water heat exchange is between the body temperature and the ice water temperature and can be assumed to be 30° C. The temperature gradient in case of air is substantially smaller, but assuming the final temperature of the exiting air as 30° C. (see Example 2), the average driving force is assumed to be 10-15° C., since the final driving force on exit from the lungs is 35−30=5° C. The likely exaggeration of the final driving force for air-lung system is offset by likely underestimated heat transfer coefficient. Since there is no actual wall between the air and lung phases (as mentioned in the Table 1), there must be a convective component increasing heat exchange, as well as a radiative component in small diameter alveoli and bronchioles. Thus, the ratio of driving forces for water-water system vs. lung-gas systems is assumed to be 2:1.

The resulting ratio of heat flows becomes:

$$[Q_{respiration}/Q_{blanket}] = [K_{respiration}/K_{blanket}][A_{respiration}/A_{blanket}][\Delta T_{respiration}/\Delta T_{blanket}] \quad (1)$$

Substitution of the numbers leads to $$[Q_{respiration}/Q_{blanket}] = (1/25)(100/1)(1/2) = 2$$

Thus, the analysis of the equation (1) shows that lungs theoretically can provide higher heat flow than an ice bath submersion or its equivalents and draws attention to precision of regulation achieved by module 30 in FIG. 4.

Example 4

Hyperventilation as a Special Regime

Assuming the lung-air heat transfer coefficient as ~15 W/m$^2$K (approximation of Table 1) and the driving force as Degrees C./K, as well as heat transfer surface of 100 m$^2$, one can obtain a heat flow of ~7.5 kJ/sec. The heat flow per 30 min becomes ~7.5*1800 sec/6=2250 kJ. The division by 6 corresponds to 10 breathing cycles per a minute, each lasting 1 sec. Assuming 3470 J/Kg C as specific heat capacity of human body, this quantity is sufficient to change the temperature of a 100 kg subject by 7.5° within half an hour. Naturally, such changes are not observable since most likely the driving force in the lungs is substantially small, due to intense upstream heat exchange. In addition, metabolic rate is assumed to be unchanged and partially compensating the heat loss between breathing cycles. On the other hand, the body loses heat to the environment through the skin surface.

One can describe the temperature drop due to the combination of factors, including ventilation as:

$$\Delta T_1 = -A_1 - A_2 V \Delta T_2 \quad (2)$$

Where
$\Delta T_1$—is the total temperature loss by the ventilated subject;
A1—is the temperature loss due to imbalance between metabolic heat production and loss through the skin;
$A_2 V \Delta T_2$—is the temperature loss due to ventilation;
V—is the ventilation volume [l/min]
$\Delta T_2$—is the temperature difference between the body core and the ventilating cold air;
$A_2$—is efficiency constant.

Based on the model (2), it is apparent that the body cooling rate is dependent on the volume of the ventilating air and the extent of air cooling.

Considering that the rate of cooling may be critical in limiting the brain damage in traumatic events and stroke, hyperventilation may allow arriving in the special most optimal regime of process parameters.

All specific regimes disclosed in the invention description are presented solely with illustrative purposes and are not limiting regarding all other possible embodiments the invention can take and known to the skilled in the art.

The invention claimed is:

1. A system for managing a body temperature of a patient, the system comprising:
   a cooler configured to lower a temperature of a breathable gas to below 0 degrees Celsius;
   a heater configured to raise the temperature of the breathable gas;
   an electronically controlled valve configured to alternately direct the breathable gas to the cooler or the heater;
   a temperature probe configured to measure the body temperature of the patient;
   a control unit in electrical communication with the electronically controlled valve and the temperature probe, the control unit being configured to control the electronically controlled valve to direct the breathable gas through the cooler or the heater depending at least in part upon the body temperature measured by the temperature probe; and
   a tube downstream of the cooler and the heater that is configured to deliver the breathable gas to the patient after it has been cooled by the cooler or heated by the heater.

2. The system of claim 1, wherein the cooler is configured to reduce the temperature of the breathable gas to −20 degrees Celsius or lower.

3. The system of claim 1, wherein the cooler is configured to reduce the temperature of the breathable gas to −30 degrees Celsius or lower.

4. The system of claim 1, wherein the cooler is configured to reduce the temperature of the breathable gas to −40 degrees Celsius or lower.

5. The system of claim 1, wherein the control unit is configured to control flow through the cooler and the heater using the electronically controlled valve in a precise sequence following patient inhalations such that a variable ratio of inhalations of cooled and heated breathable gas is maintained.

6. The system of claim 1, wherein the tube comprises an endotracheal tube configured to be inserted into the patient's trachea.

7. The system of claim 1, further comprising a source of carbon dioxide configured to add carbon dioxide to the breathable gas that is cooled by the cooler.

8. The system of claim 7, further comprising a carbon dioxide sensor configured to measure a concentration of carbon dioxide within the breathable gas after the breathable gas exits the cooler.

9. The system of claim 8, further comprising an end-tidal carbon dioxide sensor configured to measure a concentration of carbon dioxide within gas exhaled by the patient.

10. The system of claim 1, further comprising a source of breathable gas configured to provide the breathable gas to the cooler and the heater.

11. The system of claim 10, wherein the source of breathable gas comprises a ventilator.

12. A method for managing a body temperature of a patient, the method comprising:
    measuring a body temperature of the patient;
    generating a flow of breathable gas;
    alternately delivering the breathable gas to a cooler or a heater using an electronically controlled valve configured to alternately direct the breathable gas to the cooler or the heater based at least in part upon the measured body temperature of the patient, wherein the cooler cools the breathable gas to a temperature below 0 degrees Celsius and the heater heats the breathable gas; and
    alternately delivering the cooled and heated breathable gas to the patient to regulate the body temperature of the patient.

13. The method of claim 12, wherein measuring a body temperature of the patient comprises measuring the body temperature with a temperature probe.

14. The method of claim 12, wherein generating a flow of breathable gas comprises generating the flow of breathable gas using a ventilator.

15. The method of claim 12, wherein cooling the breathable gas comprising cooling the breathable gas to a temperature of −20 degrees Celsius or lower.

16. The method of claim 12, wherein cooling the breathable gas comprising cooling the breathable gas to a temperature of −30 degrees Celsius or lower.

17. The method of claim 12, wherein cooling the breathable gas comprising cooling the breathable gas to a temperature of −40 degrees Celsius or lower.

18. The method of claim 12, wherein delivering the cooled breathable gas to the patient comprises delivering the cooled breathable gas to the patient in a manner in which the patient is placed into hyperventilation.

19. The method of claim 18, further comprising adding carbon dioxide to the breathable gas before the breathable gas is delivered to the patient.

20. The method of claim 19, further comprising measuring a concentration of carbon dioxide within the breathable gas.

21. The method of claim 20, further comprising measuring a concentration of the carbon dioxide within gas exhaled by the patient.

22. The method of claim 21, further comprising controlling the amount of carbon dioxide added to the breathable gas so as to maintain a partial pressure of carbon dioxide ($pCO_2$) for the patient of 35 torr to 45 torr.

* * * * *